(12) United States Patent
Bushaw et al.

(10) Patent No.: US 8,477,304 B2
(45) Date of Patent: Jul. 2, 2013

(54) SYSTEM AND METHOD FOR HIGH PRECISION ISOTOPE RATIO DESTRUCTIVE ANALYSIS

(75) Inventors: Bruce A. Bushaw, Richland, WA (US); Norman C. Anheier, Richland, WA (US); Jon R. Phillips, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 129 days.

(21) Appl. No.: 13/050,546

(22) Filed: Mar. 17, 2011

(65) Prior Publication Data

US 2011/0164248 A1    Jul. 7, 2011

Related U.S. Application Data

(63) Continuation-in-part of application No. 12/831,985, filed on Jul. 7, 2010, now abandoned.

(60) Provisional application No. 61/223,795, filed on Jul. 8, 2009.

(51) Int. Cl.
*G01J 3/30*    (2006.01)

(52) U.S. Cl.
USPC .......................................................... 356/318

(58) Field of Classification Search
USPC .......................................................... 356/318
See application file for complete search history.

(56) References Cited

U.S. PATENT DOCUMENTS 4,707,133 A * 11/1987 Roberts et al. ................. 356/320
7,452,703 B1 * 11/2008 Czerwinski et al. ........... 435/168
7,821,634 B2 * 10/2010 Dillon et al. ................... 356/318

FOREIGN PATENT DOCUMENTS

WO    2004019020 A1    3/2004

OTHER PUBLICATIONS

Runge, E. F., et al., Spectrochemical analysis using a pulsed laser source, Spectrochimica Acta, vol. 20, Issue 4, 1964, 733-736.
Russo, Richard E., et al., Laser ablation in analytical chemistry—a review, Talanta 57, 2002, 426-451.
Simon, K., et al., Microanalysis of minerals by laser ablation ICPMS and SIRMS, Fresenius J. Anal. Chem., 359, 2997, 458-461.
Zamzow, Daniel S., et al., Insitu Determination of Uranium in Soil by Laser Ablation-Inductively Coupled Plasma Atomic Emission Spectrometry, Environ. Sco. Technol., 28, 1994, 352-358.
Smith, B. W., et al., Measurement of uranium isotope ratios in solid samples using laser ablation and diod laser-excited atomic fluorescence spectrometry, Spectrochim Acta B 54, 1999, 943-958.
Quentmeier, A., et al., Measurement of uranium isotope ratios in solid samples using laser ablation and diod laser-atomic absorption spectrometry, Spectrochimica Acta Part B 56, 2001, 45-55.

(Continued)

*Primary Examiner* — Tarifur Chowdhury
*Assistant Examiner* — Abdullahi Nur
(74) *Attorney, Agent, or Firm* — James D. Matheson; Derek H. Maughan

(57) ABSTRACT

A system and process are disclosed that provide high accuracy and high precision destructive analysis measurements for isotope ratio determination of relative isotope abundance distributions in liquids, solids, and particulate samples. The invention utilizes a collinear probe beam to interrogate a laser ablated plume. This invention provides enhanced single-shot detection sensitivity approaching the femtogram range, and isotope ratios that can be determined at approximately 1% or better precision and accuracy (relative standard deviation).

19 Claims, 8 Drawing Sheets

OTHER PUBLICATIONS

Liu, H., et al., Diode laser absorption measurement of uranium isotope ratios in solid samples using laser ablation, Spectrochimica Acta Part B 57, 2002, 1611-1623.

Koch, J., et al., Narrow and broad band diode laser absorption spectrometry—concepts, limitations and applications, Spectrochimica Acta Part B 57, 2002, 1547-1561.

Aigner, et al, International Target Values 2000 for Measurement Uncertainties in Safeguarding Nuclear Materials, Esarda Bulletin No. 31, 2000, p. 51.

Than, Nguyen Thi Kim, et al., Laser-based double beam absorption detection for aggregation immunoassays using gold nanoparticles, Anal. Bioanal. Chem. 374, 2002, 1174-1178.

International Search Report/Written Opinion, International Application No. PCT/US2010/041357, International Filing Date Jul. 8, 2010, Date of Mailing Nov. 5, 2010.

Bushaw, B. A., et al., Isotope ratio analysis on micron-sized particles in complex matrices by Laser Ablation-Absorption Ratio Spectrometry, Spectrochimica Acta Part B: Atomic Spectroscopy, New York, NY, US, vol. 64, No. 11-12, Nov. 1, 2009, pp. 1259-1265.

Liu, H. et al., Diode laser absorption measurement of uranium isotope ratios in solid samples using laser ablation, Spectrochimica Acta Part B: Atomic Spectroscopy, New York, NY, US, vol. 57, No. 10, Oct. 15, 2002, pp. 1611-1623.

Quentmeier, A., et al., Measurement of uranium isotope ratios in solid samples using laser ablation and diode laser-excited atomic absorption spectrometry, Spectrochimica Acta Part B. Atomic Spectroscopy, New York, NY, US, vol. 56, No. 1, Jan. 16, 2001, pp. 44-55.

Smith, B. W., et al., Measurement of uranium isotope ratios in solid samples using laser ablation and diode laser-excited atomic fluorescence spectrometry, Spectrochimica Acta Part B: Atomic Spectroscopy, New York, NY, US, vol. 54, No. 5, Jun. 14, 1999, pp. 943-958.

Wizeman, H. D., et al., Isotope Selective Element Analysis by Diode Laser Atomic Absorption Spectrometry, Mikrochimica Acta, Springer Verlag, Vienna, vol. 129, No. 3/4, Jan. 1, 1998, pp. 209-216.

Wendt, K. D. A., et al., Laser Based Technicques for Ultra Trace Isotope Production, Spectroscopy and Detection Hyperfine Interactions, Kluwer Academic Publishers, vol. 162, No. 1-4, Mar. 22, 2006, pp. 147-157.

De Oliveira, O. P., et al., Evaluation of the $n(^{235}U)/n(^{238}U)$ isotope ratio measurements in a set of uranium samples by thermal ionization mass spectrometry, International Journal of Mass Spectrometry, Elsevier Science Publishers, Amsterdam, NL, vol. 246, No. 1-3, Nov. 1, 2005, pp. 35-42.

Levine J. et al., Resonance ionization mass spectrometry for precise measurements of isotope ratios, International Journal of Mass Spectrometry, 288, 2009, pp. 36-43.

* cited by examiner

SYSTEM AND METHOD FOR HIGH PRECISION ISOTOPE RATIO DESTRUCTIVE ANALYSIS

CROSS REFERENCE TO RELATED APPLICATION

This application claims priority from U.S. patent application Ser. No. 12/831,985 filed Jul. 7, 2010 which claimed priority from provisional patent application No. 61/223,795 filed 8 Jul. 2009. The contents of each of these two applications are hereby incorporated in their entirety.

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The present invention relates generally to the determination of relative amounts of two isotopes. More particularly, the invention relates to a system and method for quickly and accurately detecting and analyzing relative isotope abundance distributions in desublimated gases, gases chemisorbed into solid complexes, dried liquids, solids, and particulate samples, and at trace levels in background matrices by Laser Ablation-Absorption Ratio Spectrometry (LAARS).

BACKGROUND OF THE INVENTION

Currently, there are several analytical methods available to obtain high-resolution isotopic analysis in various complex matrices including, Secondary Ion Mass Spectrometry (SIMS), Thermal Ionization Mass Spectrometry (TIMS), Inductively Coupled Plasma Mass Spectrometry (ICP-MS), and Gas Source Mass Spectrometry (GSMS). Sample analysis using these methods is generally conducted by Destructive Analysis (DA). These laboratory-based analytical methods are commonly used to support nuclear material accountancy in a gaseous centrifuge enrichment plant (GCEP), for example U-235 relative abundance determination in gaseous and solid uranium samples. The gold standard for U-235 abundance determination is laboratory-based TIMS and GSMS. While these laboratory measurements are very accurate (±0.1% for low-enriched uranium [LEU] by TIMS, ±0.05% for $LEUF_6$ by GSMS), they are encumbered by the high costs of the instrumentation, supporting facility infrastructure, chain of custody requirements for sample transport from GCEP to the offsite laboratory, and labor costs associated with the highly skilled technicians and scientists who are involved in the sample preparation, instrument operation, maintenance, and data analysis. Gaseous $UF_6$ DA requires a relatively large quantity (10-20 grams) of sample for analysis. Samples shipped offsite are transported as regulated radiological materials and create a significant radiological disposal requirement at the analytical laboratory. The timescale between sample collection and reporting of the analysis results can be up to 9 months. The large per-sample expense and analysis timescale restricts DA sampling at a GCEP as a practical matter. In the case of new, large capacity facilities, this restriction may cast doubt on whether a fully effective DA sampling plan is possible. Further, effective DA sampling plans may have operational and safeguards advantages in other facilities that support the nuclear fuel cycle—such as fuel fabrication, nuclear power, fuel processing, and waste plants.

Accordingly, it would be ideal to have a device and method to quickly collect, detect, and accurately analyze the relative amounts of uranium isotopes (e.g., U-235 and U-238) and lanthanide and other actinide isotopes in de-sublimated gases, gases chemisorbed into solid complexes, dried liquids, solids, metals, environmental particulates, aerodynamic particles, and combinations of these sample types at trace levels, and in the presence of complex background matrices. Further, it would be beneficial to have a device that is capable of automatically collecting, detecting, and analyzing such measurements. Further, it would be beneficial to have a device that is relatively inexpensive and capable of making onsite measurements with abundance precision approaching or exceeding conventional analytical laboratory methods, while using smaller sample sizes. The present invention meets these needs.

SUMMARY OF THE INVENTION

The present invention includes a system and method for obtaining high precision isotope ratio determination at high measurement spatial resolution and fast analysis time. The method includes vaporizing a sample containing at least two isotopes of the same chemical element with a laser ablation pulse oriented perpendicular to the surface in a direct optical path to form a vaporization plume. The sample is placed, collected, deposited, or chemisorbed on a solid substrate surface and is then ejected from the surface of the sample in a vaporization plume. At least one pair of diode laser beams for analyzing one isotope ratio (e.g., U-235/U-238), or multiple pairs for multiple simultaneous isotope ratios (e.g., U-235/U-238 and relative abundances of U-234 and/or U-236), are aligned to form an overlapping collinear beam that intersects the vaporization plume along a preselected 2-dimensional plane. The collinear beam is transmitted through the vaporization plume and separated into individual component beams. The absorption of the at least two isotopes is determined by comparing transmitted intensities for each of the individual component beams just prior to the ablation pulse and at a time thereafter, preselected for optimum atomic absorption characteristics. Isotope ratios can be determined for each of many preselected, spatially distinct sample areas on the substrate surface. The isotope ratios of unknown analytes, measured within the sample areas are compared with a known isotopic composition in the reference areas, and allows for unambiguous determination of the unknown isotope ratios at approximately 1% or better precision and accuracy (relative standard deviation), given a minor isotope abundance greater than a few percent, and sample quantity about a few micrograms. In general terms, analytes can include, e.g., unknowns, reference materials, measurement blanks, and other analyte types.

The invention can obtain results from a large variety of sample types. These include but are not limited to, de-sublimated gases, gases chemisorbed into solid complexes, dried liquids, solids, metals (generally greater than 1 microgram sample quantities), environmental particulates (greater than 1 micron diameter), aerodynamic particles (typically in the range of 1 to 10 micron diameter), and combinations of these sample types. More particularly, samples can include lanthanide isotopes, actinide isotopes, and combinations of these isotopes. Other isotopes and combinations of isotopes, such as gadolinium used in this invention's feasibility study, can also be analyzed by the invention. Samples can further include any isotope, distribution of isotopes, or single or multiple isotope pairs, with resolvable wavelength shifts larger than the Doppler-broadened widths in their respective atomic transitions. Sources of isotopes are also not limited. For example, uranium isotopes can be sampled from a uranium conversion, enrichment, and fuel fabrication process, collected from environmental samples, collected directly from a uranium hexafluoride cylinder, or derived from a mixed oxide (MOX) fuel process.

The invention allows samples to be analyzed as-received without prior chemical manipulation or preparation in order to achieve a preselected chemical state prior to analysis. In some applications a simple sample collection step may also be included prior to vaporization of the sample. Samples are preferably collected on substrates that exhibit strong absorption at the wavelength emitted by the selected ablation laser. Sample substrates media successfully used with this invention have included vitrified glassy carbon planchets, metallic foils, and polymer photo-mounting tapes, but the invention is not limited to such substrates as there are other absorbing materials that could be used as suitable substrates as known by those skilled in the art for the particular analyte. In one embodiment, gaseous uranium hexafluoride is collected by desublimation onto a cold finger within a reduced atmosphere chamber. In another embodiment, gaseous uranium hexafluoride is collected onto a chemical absorbent surface that binds the gaseous uranium hexafluoride thereto or that reacts through a chemisorption process, using solid chemical absorbent media (for example sodium fluoride) to yield a stable, solid complex (for example $2NaF-UF_6$). In yet another embodiment, uranium bearing particles are collected using an integrated aerosol collection system or method. In yet another embodiment, uranium bearing material is collected from swipe samples, liquid samples, or other solid hulk samples. Sample sizes for precision isotope ratio analysis of bulk materials are preferably selected to contain between about 1 µg and 5 µg of the major isotope of the targeted isotope pair, but are not limited to such quantities.

Vaporization is performed with a focused, pulsed ablation laser beam that includes use of a preselected laser wavelength, a preselected pulse energy, a preselected pulse repetition frequency, a preselected focused spot-size, and combinations of these elements. In one embodiment, the sample is vaporized in a reduced pressure, inert (e.g., argon) environment to control the size and geometry of the vaporization plume. Vaporizing can also be performed in the presence of a flowing cover gas configured for laminar flow, positioned above and parallel to the sample plane that prevents cross-contamination of sample and reference material. In a preferred embodiment, the sample is vaporized using a wavelength of 1064 nm, a pulse repetition frequency preferably between about 75 Hz and about 1000 Hz or greater, a triggered laser pulse with an energy between about 0.1 mJoules and about 1.0 mJoules, a pulse duration of about 1 nanosecond, a focused spot size with a diameter between about 10 microns and about 50 microns, and feedback isolation that prevents pulse-to-pulse timing jitter and amplitude instability. The sample can be vaporized in an "as-received" state, meaning it can be vaporized absent any prior chemical manipulation or preparation to achieve a preselected chemical state.

In a preferred embodiment, collinear overlapping laser beams are formed from wavelength stabilized, external-cavity or distributed-feedback lasers. While this example is provided, it is to be understood that it is not limited and that other types of thermally and/or optically stabilized laser sources can also be utilized. The preferred lasers have a narrow, non-overlapping linewidth less than about 20 MHz that is significantly smaller than the ~1 GHz linewidth of each target isotope and the ~20 GHz isotope shift. At least two lasers operating at different frequencies are centered on different, isotope-specific atomic absorption transitions and optionally at least one laser having selected non-resonant frequencies for background absorption correction. Each of the frequencies in the spatially overlapping probe beam can be tuned to an absorbance wavelength of a preselected isotope. The beam is of a sufficiently narrow diameter to intersect the central region of the vaporization plume along a preselected X-Y plane. The alignment of the at least two overlapping diode laser beams uses a collinear beam alignment process that ensures that the at least two component beams intersect the same volume and atom distributions within the laser vaporization plume.

In one embodiment, at least two overlapping diode laser beams are used to measure the U-235/U-238 isotope ratio in the vaporization plume using laser wavelengths selected from near 405 nm, 415 nm, 778 nm, 861 nm, and combinations thereof. Preferably, the first laser uses a wavelength of about 405 nm or 778 nm (U-238), and the second laser employs a wavelength of about 415 nm or 861 nm (U-235). In such a configuration an additional probe laser can be used for a background channel, measuring non-resonant background absorption at a wavelength near (but still separable by simple diffractive optics) the transition wavelength used for the minor isotope. An optimized implementation would use 778 nm (U-238), 861 nm (U-235), 855 nm (background); all are wavelengths produced by commercially available distributed feedback (DFB) diode lasers that are compact, reliable, have low power consumption, and are relatively inexpensive.

In another embodiment, aligning at least two overlapping diode laser beams using a strong atomic transition for a minor isotope and weaker transition for a major isotope to enhance the dynamic range of the relative abundance measurement. The alignment also includes directing an overlapping collinear beam so that it is oriented parallel to the sample plane and includes a prescribed offset relative to the sample plane. The method can be used to conduct a uranium and/or plutonium isotope analysis.

The present invention provides the ability to detect and discriminate non-resonant absorbance events. The determining step includes calibrating the relative isotope abundance for each of the at least two isotopes using an internal calibration standard with a preselected isotope distribution and a preselected chemical form. This includes calculating corrected absorbencies for each of the at least two isotopes measured in the vaporization plume, determining enrichment alarm thresholds for selected isotopes measured in the vaporization plume, and comparing transmitted intensities before and after the laser ablation pulse. The comparing step is preferably performed at or near the time of maximum transient absorption on a shot-by-shot basis. The comparing step includes moving the sample laterally underneath a ablation laser, and at least two probe lasers (used for generating the ablation pulse and collinear beam, respectively) to construct absorbance images and isolate data corresponding to specific positions or areas on the sample surface. The determining step includes use of a raster scan pattern defined by a preselected (sweep x, step y).

Once this data has been collected statistical analysis on shot-by-shot and raster line-by-line absorption data for specified sample area scan then be performed. This may include determining isotope ratios and statistical uncertainties for the sample areas. The present invention provides for up to a femtogram sensitivity for the minor isotope abundance. The method further includes generating timing signals that precisely control acquisition of the pre-vaporization background, the post-vaporization signal for the transmitted laser beam, and their preselected timing delays, timing offsets, and averaging controls. The method further includes use of a burst mode analog-to-digital absorbance signal to facilitate rejection of false signals due to non-resonant absorption events and to provide integrated absorbance measurements. The method is used to isotopically analyze a singular sample element of a preselected spot size or dimension. The method is used to isotopically analyze more than one sample element of a preselected spot size or dimension. The method can be performed iteratively to isotopically analyze an entire sample at a preselected spot size or dimension. The iterative analysis provides a collection of individual pixels that provides isotopic analysis of same. The iterative analysis can include scanning the sample using a scanning method selected from the group consisting of: raster scanning, optical scanning, mechanical scanning, optical-mechanical scanning, micro-electro mechanical scanning, and combinations thereof at a spatial resolution of at least 20 µm.

The invention provides at least a factor 10 better precision compared to standard laser-based ablation sample analysis systems known in the prior art. Particularly when performed on solid samples with an unknown abundance that are run side-by-side with a known calibration reference. Both the sample and reference materials are scanned rapidly using interleaved spatial measurements in a timed-sequenced format so that both the unknown sample and calibration reference are measured for every 'line' of the rasterized scan. This provides near real-time normalization of the instrument response which corrects for systematic errors including, e.g., laser frequency drift and pointing errors that are problematic to, and characteristic of, laser-based systems which have limited the performance of prior art systems.

The present invention has significant advantages, including rapid, high precision isotope analysis that requires minimal sample material and U-235 relative mass. The present invention has demonstrated ±0.9% relative standard uncertainty of U-235 abundance relative to U-238, with femtogram sensitivity for the minor isotope using $\leq 1$ microgram sample quantities for 2.5% low enriched uranium. It is expected that the relative standard uncertainty can be further improved by at least a factor of 10.

The method of the present invention allows for the testing of a variety of samples which can be collected in a variety of ways. The present invention is particularly effective in testing samples that contain materials such as actinide isotopes whether collected in any of a variety of methods. In one application the sample is collected from a gaseous uranium hexafluoride source. Such a collection may be obtained by use of a chemical absorbent media to produce a stable, solid complex or by desublimation onto a cold finger or by any other means readily available and ascertainable by a party of skill in the respective fields. The present invention finds particular application in performing collection and analysis of materials such as those found from leakage from uranium hexafluoride production equipment, for example, obtained during uranium hexafluoride production operations and/or from, a uranium hexafluoride storage cylinder and associated equipment. Such an invention thus is particularly useful in fields and applications such as safety, material accountancy/safeguards at gaseous centrifuge plants, laser separation plants, production facilities, and other applications. The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

BRIEF DESCRIPTION OF THE DRAWINGS

A more complete appreciation of the invention wilt be readily obtained by reference to the following description of the accompanying drawings in which like numerals in different figures represent the same structures or elements.

DETAILED DESCRIPTION OF THE INVENTION

Figure 1:
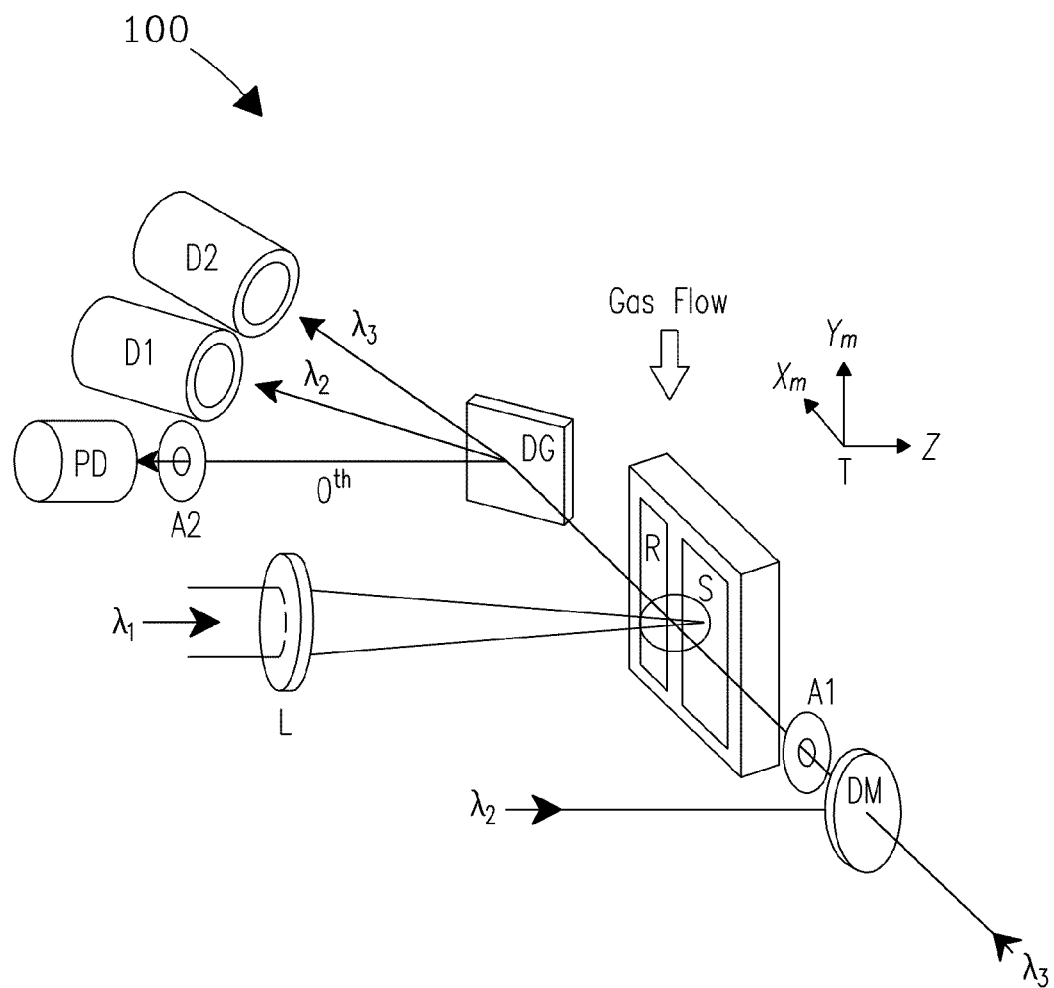
FIG. 1 shows a schematic embodiment of one embodiment of the invention.

A system and process are disclosed that provide high precision isotope ratio determination at high measurement spatial resolution and fast analysis time for destructive analyses for isotope ratio determination of relative isotope abundance distributions in collected gases, liquids, solids, and particulate samples. As used herein, the term "destructive analysis" (DA) means an analysis which consumes sample material and/or changes sample morphology and where the sample being measured is not returned to the batch it was taken from. The term encompasses analyses of bulk samples including, e.g., uniform liquids or solids where repeat analyses may be performed with replicate aliquots. In addition, analyses of non-uniform samples (e.g., atmospheric particulate collections) generically referred to as "Environmental Samples" (ES) herein can also be performed.

The term "high spatial resolution" as used herein refers to the ability to resolve individual particles in various complex sample matrices. High spatial resolution measurements typically require three things: 1) a small ablation spot size (< about 20 um), 2) a scanning system and platform that provide sufficient resolution (< about 20 um), and 3) measurement sensitivity sufficient to determine the quantity of material within the selected spot size at the stated resolution.

The invention is faster and more accurate than laser spectroscopy systems and methods known in the conventional analytical art. It reduces analysis time for complex samples from hours to fractions of an hour (~15 minutes) compared to conventional laser ablation spectroscopy. Precision for particle assays has also been demonstrated to be better than 10% on particles as small as 1 um. Minor isotope sensitivity has also been demonstrated to be in the femtogram range. The invention is expected to provide a dative abundance dynamic range for LAARS measurements, e.g., for uranium particulate assays, that spans the range from those containing depleted uranium (DU) to those containing highly enriched uranium (HEU), and all enrichment levels in-between. For example, results to date indicate that a few highly enriched uranium (HEU) particles can be identified among 10,000s of natural uranium particles. In addition, a few particles containing HEU can be identified among 10,000,000s of "dust" particles.

As described in the summary section, the invention employs laser vaporization, to prepare the sample, and optimized substrate media to enhance the laser vaporization process. Probing a collinear beam made up of two beams from two single-mode wavelength-stabilized spectroscopy lasers that have narrow, non-overlapping linewidths that are significantly smaller than the atomic absorption linewidth and isotope shift, are used to simultaneously measure, and ratio, the two targeted isotopes. The isotope abundance analysis requires only femtograms of the minor isotope for single point abundance determinations and only microgram samples for destructive assay. Isotope abundance determination (e.g., for U-235 abundance) is made on a shot-by-shot basis up to 1 kHz, with a precision value better than 1.0% on average for bulk, homogeneous samples having at least 3% relative minor abundance. The invention requires no pre- or post-vaporization sample preparation and requires significantly less sample material and preparation compared to traditional analytical methods used for both ES and DA measurements. The system and method of the invention are applicable to isotope ratio determination for a large number of elements including, but not limited to, e.g., lanthanides and actinides. However, it should be strictly understood that no limitations to the invention are intended by the description to exemplary elements and isotopes herein.

The following description and figures describe various preferred embodiments of the present invention. It will be clear from this description of the invention that the invention is not limited to these illustrated embodiments but that the invention also includes a variety of modifications and embodiments thereto. Accordingly, the following description of the invention should be seen as illustrative of the invention and not as limiting in any way.

Referring now first to FIG. 1, FIG. 1 shows a schematic of one embodiment of the present invention. In operation, a sample either a reference R or a sample S is positioned upon a substrate preferably within a sample chamber whereupon the ablation laser beam $\lambda_1$ is focused upon the sample and vaporizes the sample to create a plume. A collinear probe beam formed by the alignment of two separate beams $\lambda_2$, $\lambda_3$ through a collimation lens DM is then directed through the plume. After passing through the plume an optical separator DG then separates the collinear beam back into two separate beams $\lambda_2$, $\lambda_3$ which are then passed on to separate detectors D1, D2 which measure a desired characteristics of the beams. By determining the difference in a preselected characteristic from a known value of the beams prior to passing through the plume and the values measured at the detectors D1, D2 an absorption value can be determined. In as much as the individual beams are targeted for specific isotopes, the quantity of absorption can be utilized to then provide statistically correlated data related to the quantity of particular isotopes within the sample.

Figure 2:
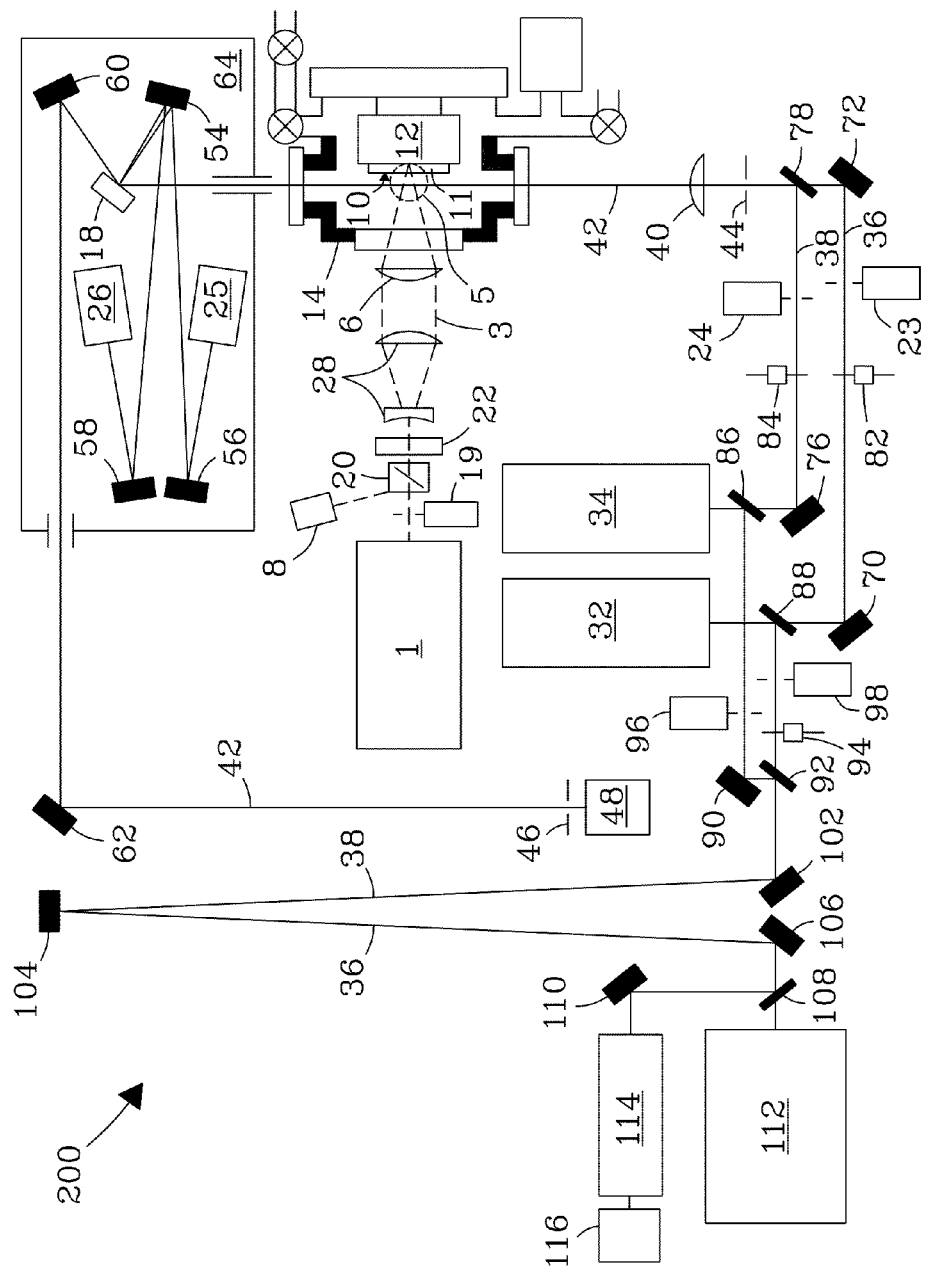
FIG. 2 shows a preferred embodiment of a LAARS laser ablation destructive sample analysis system that provides high precision, isotopic ratio determination in accordance with the invention.

More detailed descriptions of the method and system of this embodiment, and specific instances of their application are shown in FIGS. 2-12 and are described in more detail hereafter. Referring now to FIG. 2, FIG. 2 shows a schematic configuration of one embodiment of the invention that performed a variety of tests which are also described hereinafter. This system 200 includes an ablation laser 1. The ablation laser 1 is in this embodiment is a diode-laser pumped, Q-switched, Nd:YAG laser, but any suitable ablation laser could likewise be utilized. This ablation laser 1 is configured to deliver an output beam 3 with a path shown by dashed lines. This output beam 3 delivers high-energy pulses at a preselected wavelength, energy, and duration to the sample 10. In this preferred embodiment these preselected values were a wavelength of 1064 nm, a pulse energy of ~0.3 mJ (300 microjoules/pulse), and a pulse duration of about 1 ns. Beam 3 further includes a pulse repetition rate between about 0 Hz and about 1000 Hz (0-1 kHz). (In this embodiment a rate between about 75 Hz and about 300 Hz was selected). The output beam 3 of ablation laser 1 is directed and configured to be tightly focused onto the surface of sample 10 using a focusing lens 6 positioned in front of ablation laser 1, which yields an ablation spot (not shown) on sample 10 of a preselected size. The diameter of the ablation spot is preferably selected, but not limited to, between about 20 μm and about 30 μm to provide a sufficiently high spatial resolution for determination of isotopes present in sample 10. A detector 8 is coupled to the polarizer 20, which is used to monitor tight scattered from polarizer 20 as it is received from ablation laser 1. Scattered light monitored at detector from polarizer 20 is further used as a timing signal and as a diagnostic for operation of ablation laser 1.

A computer-controlled shutter 19 located in front of ablation laser 1 is used to block or expose sample 10 to output beam 3. Ablation laser 1 is further configured with anti-reflection-coated polarizer 20 (e.g., a Glan-Thompson polarizer, New Focus, Inc., Santa Clara, Calif., USA) and an anti-reflection-coated quarter-wave ($\lambda/4$ plate) retarder 22 (New Focus, Inc., Santa Clara, Calif., USA), Polarizer 20 and quarter-wave retarder 22 collectively define an optical isolator that prevents spurious specular reflections from destabilizing ablation laser 1. Output beam 3 is expanded through a diffraction-limited-beam expander 28 (e.g., a 10× beam expander, Thorlabs, Newton, N.J., USA). In this exemplary embodiment, focusing lens 6 is preferably mounted onto a linear Y-Z translation stage configured with both a Y-direction fine adjustment (not shown) and a (Z-direction focal depth adjustment (not shown) that provide for centering of the ablation spot on sample 10, e.g., at a height identical to that selected for the collinear probe beams (36, 38) delivered from probe lasers (32, 34), as described further herein. The person of ordinary skill in the art will recognize that additional optical components including, but not limited to, e.g., focusing lenses, shutters, polarizers, waveplates, beam expanders, and like optical components may be used without limitation to direct and focus laser beam 3 from ablation laser 1 onto sample 10. No limitations are intended.

The sample 10 can be any of a variety of sample types as described here after. However, solids samples are generally preferred. These solid samples are generally placed upon an X-Y-Z sample translation stage 12 that controls translation of sample 10 in both the X and Y dimensions underneath focused beam 3 of ablation laser 1 as ablation laser 1 propagates along the Z axis. Sample 10 is preferably mounted onto a preselected solid substrate (e.g., 1-inch flat round wafer), which is then placed onto translation stage 12. The X and Y axes define the sample surface plane. Sample translation stage 12 permits the surface of sample 10 to be raster-scanned under computer control. In the exemplary embodiment, translation stage 12 is driven by miniature encoded DC-motors (e.g., Model MM-3F, Numerical Aperture, Inc., Salem, N.H., USA) that are under computer control, but configuration is not limited thereto. Translation velocity of stage 12 is typically about 6 mm/s, but speed is not limited. Sample 10 is axially translated approximately one laser spot size before a subsequent measurement. Translation and ablation laser spot sizes are nominally 20 μm. Thus, about 20 μm of the X-axis position is translated on average for each pulse fired from ablation laser 1, which provides the necessary spatial resolution for isotope analysis.

Each time ablation laser 1 fires, one spatial location on the XY plane of sample 10 is vaporized and measured. A 'line' of ablation shots is thus taken while sample 10 is translated underneath ablation laser 1 in the X-direction. Translation continues along the X-axis until the end of the selected row is reached. At the end of each scan line, sample 10 is translated in the Y dimension by a 'step' of approximately one to four oblation beam diameters (e.g., from about 20 μm to about 80 μm), which advances the sample incrementally in the Y-direction to the next row, where the X-dimension is then retraced to the starting position without ablation laser 1 firing. The process is repeated until the entire plane of sample 10 is vaporized and/or isotope signals are analyzed.

At the end of an experiment, a data array is compiled composed of XY coordinates from many multiples of absorbance amplitude spatial locations obtained from each isotope channel, from which a computer-generated raster scan image of the surface of sample 10 is subsequently generated. Translation stage 12 provides a resolution of at least about 1-micron. At this resolution, system 200 provides a measurement sensitivity for minor isotopes that is on the order of femtograms.

The term "sample" as used herein in reference to the invention refers to analyses in which both an unknown component and a reference material are measured. The term also applies to analyses of materials that contain at least one unknown component. Sample (S) and reference (R) materials are preferably mounted in designated areas, e.g., side-by-side, although location is not limited. Suitable substrates for mounting samples 10 provide strong absorptive properties that trigger or promote the laser vaporization by: 1) enhancing the amount of material removed from the substrate, 2) affecting the plasma temperature, 3) effecting ion yield, or 4) effecting resulting dissociation properties necessary to form an atomic vapor for the targeted element. Translation stage 12 allows the surface of sample 10 positioned on solid substrate 11 to be raster-scanned underneath ablation laser 1. In the raster scan, each line in the X-dimension (completed, e.g., every few seconds) includes both a sample (S) region (i.e., having unknown target element concentrations and isotope abundances) and a reference (R) region. Rapid interleaving between sample (S) and reference (R) measurements minimizes systematic errors common to laser-based isotope analyses including, e.g., probe laser pointing and alignment errors, overlap errors, frequency setting errors, and laser drift errors.

In the preferred embodiments of the invention, glassy carbon substrates were determined to yield a significantly stronger and more stable signal than other sample substrates including, e.g., metal foils or polymer tapes. Glassy carbon substrates also allow multiple samples to be placed on a single measurement surface which allows for high throughput analyses and use of internal standards. In one embodiment, a single measurement planchet composed of glassy carbon can be constructed that includes multiple locations (e.g., exposed 'chips', or shallow wells) for mounting samples. Number of sample locations is limited only by the size of the mounting surface. In an exemplary configuration, the planchet can include, e.g., ~100, 2-mm square locations, plates, or wells for mounting particulate samples or dried liquid samples, but number is not limited. In addition, the planchet can include internal standards (e.g., known reference materials) that are placed among any one or more of the multiple unknown samples to normalize systematic variations associated with laser drift including, but not limited to, e.g., frequency, pointing, side-mode structure, and like variations, in one preferred embodiment independent 'stripes' of sample (S) and reference (R) material are placed side-by-side on a single substrate, so as to generate a series of interleaved sample and reference measurements (e.g., separated, e.g., by only a few seconds) collected during the raster scan with the ablation laser. This embodiment provides significant cancellation of many systematic errors and drifts, which is important in reaching desired accuracy in relative isotope ratio determination. This embodiment further provides high measurement confirmation value, failure detection, and detection of disruptions in unattended instrument operation.

In addition to these methods of sample preparation other methods have been employed as well. For example liquid (aqueous) samples are generally dropped (5-50 microliters typical) on to a sample carrier surface and dried in an oven. Aluminum and titanium foils and vitreous carbon planchets (carbon discs) have been successfully used as carriers for liquid samples. Vitreous carbon, with a matte finish, is a preferred sample carrier because strongly absorbs ablation laser tight, which provides strong and fairly uniform laser vaporization plumes. Arrays of dried drops are routinely used. And, multiple samples and references can be loaded and measured on a single sample carrier. Plastic tips of a loading pipette can be used to 'paint' the liquids or drops into long stripes on a warmed carrier surface while drying, which gives more uniform sample loading. This is also a preferred method for side-by-side comparisons of sample and reference samples for high-precision isotope abundance measurements.

Referring now back to FIG. 2, in this embodiment two single-mode, tunable diode lasers (32, 34) deliver respective probe beams (34, 36) that are collimated to create a probe (interrogate) vaporization plume 5 generated by ablation laser 1. Probe beams (36, 38) propagate above the surface of sample 10 parallel to the X-axis. Probe lasers (32, 34) each couple to a linear Y-Z translation stage 30 (not shown) that permits height of probe beams (36, 38) to be adjusted in the Z-dimension to a height above the surface of sample 10.

The system 200 further includes a (e.g., 50 cm focal length) collimation lens 40 that collimates probe beams (36, 38) into a single collinear probe beam 42. A first alignment aperture 44 with an adjustable iris (~0.3 mm operating diameter, not shown) is positioned adjacent to collimation lens 40 to align the first probe beam 36 delivered from first probe laser 32. A second alignment aperture 46 is positioned adjacent to beam alignment detector 48 (e.g., a Si-PIN amplified photodiode, Thorlabs, Newton, N.J., USA) and also includes an adjustable iris (~0.3 mm operating diameter, not shown) that is used to align the second probe beam 38 received from second probe laser 34. Beam alignment detector 48 monitors the power of collinear probe beam 42 delivered through second alignment aperture 46. In the exemplary embodiment, beam alignment detector 48 is an amplified photodiode (e.g., a Si-PIN photodiode), but is not limited. Distance of collimation lens 40 from first alignment aperture 44 is preferably adjusted to minimize the spot size (e.g., ~20 µm) of collimated probe beam 42 delivered at second alignment aperture 46, but is not limited. Computer-controlled shutters (23, 24) positioned in line with respective probe lasers (32, 34) prevent probe lasers (32, 34) from measuring baseline offsets of beam detectors (25, 26). In operation, one shutter 23 is closed and one shutter 24 is opened (or vice versa) to select one of probe beams (36, 38) as the primary optical axis for transmission (i.e., overlap alignment) of collinear probe beam 42. In operation, alignment apertures (44, 46) are opened (~6 mm) to allow initial passage of collimated probe beam 42. A holographic (e.g., 3600 line/mm) diffraction grating 18 positioned in the optical path of collinear beam 42 after it passes through vaporization plume 5, separates beam 42 back into probe beam wavelengths. High-reflectivity mirror 54 receives the separated probe beams (50, 52) as $1^{st}$-order reflection beams from diffraction grating 18. High-reflectivity folding mirrors (56, 58) increase the separation of separated probe beams (50, 52) delivered from diffraction grating 18 and deliver these separated probe beams (50, 52) into respective detectors (25, 26) for detection. In an exemplary, implementation, detectors (25, 26) are photomultipliers of a compact, high-voltage (i.e., +12 VDC) type configured with built-in conversion for detecting transmission of separated probe beams (50, 52) downstream from laser vaporization plume 5. Low-noise current amplifiers (not shown) may be coupled to increase and/or stabilize output signals delivered from detectors (25, 26).

System 200 employs two additional high reflectivity mirrors (60, 62). A first high reflectivity mirror 60 receives collinear beam 42 from holographic grating 18 as a $0^{th}$-order reflection beam. As the $0^{th}$-order reflection of beam 42 does not have a wavelength-dependent direction, probe beams (36, 38) that comprise collinear beam 42 remain unseparated therein. The unseparated, $0^{th}$-order reflection beam 42 is directed via a second high-reflectivity mirror 62 through second alignment aperture 46 to beam alignment detector 48, which monitors the power of collinear beam 42, as described previously herein. In one exemplary implementation for measurement of uranium isotopes, probe lasers (32, 34) can include external cavity violet diode lasers that are tuned to wavelengths near 405 nm and 415 nm, respectively. In another implementation, a red diode laser, tuned to a wavelength near 778 nm, can also be used to provide a similar sensitivity for determination of uranium. The transition near 861 nm for uranium is also known to be twice as strong as the 778 nm transition.

In a preferred embodiment, distributed-feedback (DFB) diode lasers (e.g., models DFB-0780-080 and DFB-0850-060 distributed-feedback diode lasers, Sacher Lasertechnik, LLC, Buena park, CA, USA) can be used for uranium isotope enrichment measurements as these lasers operate in a stable and tunable, single mode at 778 nm and 861 nm without mechanical tuning elements.

Two high reflectivity mirrors (70, 72) are used as a periscope to spatially orient probe laser beams (36, 38) that assists in the alignment of probe lasers (32, 34). In particular, periscope defines the position or starting point of one (e.g., first) probe laser beam 36 on the surface of second periscope mirror 7 and the direction of laser beam 36 as defined by the angular adjustment of the second periscope mirror 72. The first periscope mirror 70 determines the origin of the beam 36 origin point on second mirror 72. Second periscope mirror 72 then defines the direction of beam 36 away from the origin point. Alignment of first probe beam 36 to form collinear beam 42 involves only pinhole apertures (44, 46) and photodiode detector 48 in addition to periscope mirrors (70, 72), and can be automated using computer controlled periscope mirror pointing. Two additional high reflectivity mirrors (76, 78) form a second periscope used to align the second probe laser 34 in conjunction with probe beam alignment apertures (44, 46).

Mirror 78 is partially reflective (~50%) to allow combination and overlap of probe beams (36, 38). Two variable neutral density filters (82, 84) of a rotatable wheel type are used to adjust power of probe beams (36, 38). Beam splitters (~10%) (86, 88) are used to monitor the wavelengths and mode structures of probe beams (36, 38). A steering mirror 90 directs probe beam 38 from probe laser 34 to beam combiner 92. Beam combiner 92 is a beam splitter (50%) that overlaps probe beams (36, 38) combining, them to form collinear beam. A variable neutral density filter wheel 94 is inserted in the path of the stronger probe beam (36, 38) to balance (equalize) power of probe beams (36, 38) in combined beam 42. Computer-controlled shutters (96, 98) are used to deliver individual probe beams (36, 38) to wavelength meter 112 and optical spectrum analyzer 114, respectively, for wavelength and/or mode monitoring of probe beams (36, 38).

A beam splitter (e.g., 50%) 108 divides collinear probe beam 42 between wavelength meter 112 (e.g., a Michelson interferometer) and optical spectrum analyzer 114 (e.g., a confocal interferometer or scanning Fabry-Perot interferometer). Wavelength meter 112 is capable of measuring wavelengths of probe laser beams (36, 38) in collinear beam with an accuracy of about 1 part in $10^7$ parts (60 MHz). This precision exceeds the Doppler broadened linewidths associated with isotope transitions in plasma afterglows (e.g., ~1 GHz). In particular, the precision allows each of the frequencies of probe lasers (32, 34) to be precisely set at the center of their selected absorption lines providing for reproducible and quantitative measurements. The signal output from wavelength meter 112 provides the basis for a digital feedback loop that stabilizes operating frequencies of probe lasers (32, 34) by removing long-term drift, described further hereafter. Three high reflectivity mirrors (102, 104, 106) are used to fold the path of the collinear beam to provide a sufficiently long path length (e.g., >1 m) for precise alignment of wavelength meter 112 positioned near the end of the beam bath. Mirrors (102, 104, 106) provide a simple alignment mechanism for aligning collinear beam with the HeNe laser alignment beam that emanates from wavelength meter 112. Alignment of wavelength meter 112 requires simply minor adjustment of mirrors 102 and 106 mirror 104 remains fixed. Beam splitter 108 is used in conjunction with a separate mirror 110 to form a periscope 112 that aligns collinear beam directly into spectrum analyzer 114.

Multiplexing with shutters (96, 98) and beam combiner (92) allows for monitoring and stabilizing both probe lasers (32, 34). An optical spectrum analyzer 114 (e.g., a scanning Fabry-Perot interferometer) monitors mode structure of probe lasers (32, 34). An amplified photodiode 116 (e.g., a Si-PIN amplified photodiode, Thorlabs, Newton, N.J., USA) monitors transmission of probe beams (36, 38) through optical spectrum analyzer 114. Another amplified photodiode 8 monitors output of ablation laser 1 via scattering from the polarizer 20. A protection box 64 positioned around probe detectors (25, 26) is a baffled light isolation box that prevents probe detectors (25, 26) from exposure to spurious or stray tight.

A cover gas (e.g., argon) can be sourced into the sample chamber 14 from, e.g., a compressed gas bottle or another suitable gas source through a valve. Additional air flow cat be used to provide a ballast volume when flushing air out of sample chamber 14. Preferably sample chamber 14 is gas-tight and is configured with windows. A vacuum or alternate pumping system, with adjustable pump out speed, is used for removal of environmental gases present within sample chamber 14 prior to an experiment. Gas (e.g., Argon) supply line is preferably introduced from the top of chamber 14 and is pumped out from the bottom of sample chamber 14 such that gas flows across the sample perpendicular to probe beam 42. This orientation and gravity further prevents cross contamination of the reference positioned side-by-side with unknown sample. A capacitance manometer was utilized to monitor gas pressure in sample chamber 14. Pressure in sample chamber 14 is adjusted preferably to about 10 Torr using a flow rate of ~10 sccm.

Sample chamber 14 is preferably mounted on a manual translation stage 30 (e.g., Z-stage) (not shown) that permits the height of probe beams (36, 38) to be adjusted above surface of sample 10 without requiring realignment of probe beams (36, 38). A quick release flange (not shown) that includes, e.g., 2 wing nuts on studs provides sample translation stage 12 with built-in feedthroughs (not shown) that house electrical conduits and cabling that deliver electrical signals for driving and reading the position of translation stage 12. Focusing lens 6 for ablation laser 1 is preferably mounted on the same translation stage 12 as sample chamber 14 such that output beam 3 that is tightly focused onto surface of sample 10 will not change when sample chamber 14 is translated. Translation stage 12 further allows for adjustment of the focal length of focusing lens 6.

A control computer (not shown) generates Transistor-Transistor Logic (TTL) pulses that fire ablation laser 1 and that trigger analog-to-digital conversions (ADC) for probe beams (36, 38) and other instrument components that employ precise timing delays timed relative to the firing of ablation laser 1. Examples of such commands include delivering a specified number of pulses, inter-pulse delay, and pulse delays (positive or negative) relative to the firing of ablation laser 1. In the exemplary implementation, only two pulses are used, but the invention is not limited thereto. For example, intensities of probe lasers (32, 34) are measured typically ~5 μs before the firing of ablation laser 1 and typically from 10 to 20 μs after the firing ablation laser 1. Intensity data collected before the firing of ablation laser 1 (i.e., before the ablation pulse) measures the baseline transmission(s) ($I_0$) before delivery of the ablation pulse. A second pulse(s) is configured with adjustable time delay that measures intensities ($I_t$) of transmissions through the vaporization plume 5 (i.e., atomic cloud of the plasma afterglow). These latter pulses are usually set to the time of maximum isotope absorbance, but can be set for later times cooler) to achieve better spectral resolution.

This approach has several advantages. First, the short time between the two intensity measurements effectively removes probe laser amplitude noise up to ~50 kHz, and significantly towers detection limits such that absorbances as low as ~$10^{-4}$ can be measured on a single-shot basis. Second, embedding the paired data in single waveforms allows very fast data acquisition and transfer, which can support ablation lasers having very high repetition rates. High repetition rates further allow both rapid and large-area sample scans at high resolution, especially useful for particle measurement applications, and further provides significant signal averaging useful for bulk analysis samples. The number of paired pulses can also be expanded to provide a burst of sampling pulses which can provide additional signal averaging, or fault analysis for each pulse. Further, imbedding multiple waveforms still allows high data transfer and ablation laser repetition rates. Transmission signals from photomultiplier detectors (25, 26) are conditioned with a low-noise current amplifier (not shown) (e.g., a SR570 low-noise current preamplifier, Stanford Research Systems, Sunnyvale, Calif., USA). Output voltages are converted by high performance analog-to-digital converters (ADCs) (e.g., non-multiplexed, simultaneous 16-bit, 800 kHz, ADCs for each input) (not shown) and read by computer, as described hereafter. Operating wavelengths (e.g., absolute frequencies) of probe lasers (32, 34) are measured with a wavelength meter 112 (e.g., a Burleigh WA-1500 wavemeter, Burleigh instruments, Inc., Victor, N.Y., USA). Wavelength meter 112 provides an output signal that includes the operating frequency that is read via an RS-232 serial communication port (not shown).

A probe beam detector (e.g., a photodiode detector) 116 monitors the fringe transmission pattern from the optical spectrum analyzer 114 for each selected probe laser (32, 34). Output voltage of the amplified photodiode 116 is read with a general purpose ADC and is processed as a virtual oscilloscope trace for monitoring purposes. Another photodiode detector (8) is used to monitor the output beam 3 of ablation laser 1. A third high performance ADC (not shown) is used to synchronize digitization with transmission detectors (25, 26). A capacitance manometer (e.g., a Baratron® capacitance manometer, MKS Instruments, Inc., Andover, Mass., USA) is used to monitor the pressure in sample chamber 14. Exemplary pressures are between about 0 Torr and about 100 Torr, but pressures are not intended to be limited. The pressure output signal is read with a general purpose ADC, which is read b, the control computer.

In use, sample 10 is vaporized by the focused ablation laser 1 that emits a vaporization plume 5 onto the surface of sample 10 placed on solid substrate 11 (not shown) (e.g., using laser-induced-plasma (LIP) formation on the solid surface), forming a laser-induced vaporization plume 5. Vaporization of sample 10 on the surface of solid substrate 11 (not shown) serves as the chemical preparation step in the analysis. Output beam 3 of ablation laser 1 is directed as a high energy laser pulse through beam expander 28 that expands the output beam 3. Output beam 3 of ablation laser 1 is tightly focused through focusing lens 6 at a normal incidence (i.e., along the Z-dimension) onto the surface sample 10 positioned on solid substrate 11 (not shown), producing an ablation spot of a diameter between about 10 μm to about 50 μm (typically ~20 micron in diameter). Pulse energy of beam 3 generates a laser-induced vaporization plume 5 containing material ablated from the surface of sample 10. Pulse energy of beam 3 is preferably selected between about 0.1 mJ/pulse and about 1 mJ/pulse, which ignites the vaporization plume 5 that ionizes measurable quantities of material in sample 10 into appropriate gas phase atomic species (e.g., ions and neutrals).

The gas phase atomic species are ejected from the surface of solid substrate 11 (not shown), providing a reservoir of gas-phase atomic species including, but not limited to, e.g., atoms, ions, and/or other molecular species representative of the sample material. These various species are then interrogated by high-resolution atomic absorption spectroscopy described hereafter. Gas phase atomic species are constrained and cooled by an inert cover gas (not shown) (e.g., argon) present at a pressure of, e.g., ~10 Torr. The initial plume 5 rapidly expands and cools as it interacts with the cover gas. As plume 5 cools, expansion of the plume slows, ions recombine with electrons to form atoms, and the background continuum plasma emission dies out. The resulting afterglow plasma remains briefly stable as species de-excite and participate in secondary chemical reactions that form atomic vapor species. The 'afterglow' plasma is a nearly hemispherical plume 5 of gaseous atoms that extend ~3-5 mm above the surface of sample 10. In one exemplary, implementation, ablation laser 1 is a short pulse Nd:YAG laser operating at a fundamental wavelength of 1064 nm. Pulse energy is ~0.3 ml. Pulse duration is ~1.5 ns. And, repetition rate is up to about 1 kHz. However, operating parameters are not limited thereto.

In order to ensure the appropriate operation of the system the beams involved must be aligned to create a desired effect, "Initial" or "first time" alignment means lasers and laser beams used in conjunction with the LAARS instrument system have not yet properly aligned, or have only been coarsely aligned for operation. "Day-to-day alignment" refers to alignment that occurs immediately prior to, or on the day of, an analysis. A description of the method required to enable such an alignment is described hereafter.

Initial Alignment. In a first step {step 1}, alignment apertures (44, 46) are opened (~6 mm) to allow initial passage of probe beams (36, 38). Shutter 23 is closed and shutter 24 is opened (or vice versa), which permits one probe beam 36 or 38 of diode laser 32 or 34 to be selected as the primary optical axis for alignment of probe beams (36, 38).

Next {step 2}, mirrors (70, 72) are used as a periscope to align beam 36 of first probe laser 32 so that it passes above and parallel to the surface of sample 10 such that it impacts near the center of holographic grating 18. Mirror 70 is used to select the source point on minor 72, and mirror 72 is used to select the direction of probe beam 36. Parallelism with the surface of sample 10 is checked by translating sample 10, or sample chamber 14 containing sample 10, mounted onto translation stage 12 (not shown) forward until the surface of sample 10 begins to clip probe laser beams (36, 38). If the surface of sample 10 and probe beams (36, 38) are parallel, scattering of probe beams (36, 38) from the surface will be fairly uniform along the length of the surface of sample 10. Position of sample chamber 14 can be adjusted on translation stage 12 (not shown) to obtain parallelism. After verifying parallelism, sample chamber 14 is retracted to allow free passage of probe beams (36, 38) ~2 mm above the surface of sample 10.

Next {step 3} the $0^{th}$-order reflection beam of collinear beam 42 from holographic grating 18 is directed from mirror 60 to mirror 62 such that it is centered onto photodiode detector 48 through second alignment aperture 46.

Next {step 4}, first alignment aperture 44 is adjusted so as to be centered approximately on a selected probe beam 36 or 38, which is then stopped down until the diameter of first aperture 44 is approximately ⅓ the diameter (~0.3 mm) of probe laser beams (36, 38) used for the alignment. Final positioning of aperture 44 is manually adjusted (e.g., using fine adjustment screws) to yield a maximum intensity at photodiode detector 48.

In another step {step 5}, second alignment aperture 46 is coarsely centered on collinear probe beam 42, which was coarsely centered in {step 4} onto detector 48 and stopped down to ~⅓ the probe beam diameter. Power of probe beam 42 transmitted through aperture 44 is maximized by monitoring the signal from photodiode detector 48. Adjustment is preferably done by pointing the beam with mirror 62, rather than translating second aperture 46. At this juncture, the geometry of probe beam 42 from first aperture 44 to second aperture 46 is defined. Optical elements (60, 62, 70, 72) are also fixed and need no further adjustment. Fine tuning of alignment between ablation laser 1, sample 10, second probe laser 34, and any further pointing adjustment to probe detectors (25, 26) is done by matching these various components to the axis of first probe beam 36.

Next {step 6} beam 38 from second probe laser 34 is passed through system 200 by opening shutter 24. Initial coarse alignment of second beam 38 is achieved by visually overlapping second beam 38 with the first beam 36 from first probe laser 32 such that they are combined at detector 48. Beam 36 from first probe laser 32 is then blocked by closing first shutter 23.

Next {step 7}, fine alignment of second probe laser 34 is accomplished. The alignment of second probe laser 34 is fine-tuned by monitoring and maximizing power at detector 48. In this step, final aperture 46 is opened to allow small pointing variations without clipping collinear beam 42. Maximum power from second probe laser 34 through first alignment aperture 44 is obtained by adjusting first periscope mirror 76 stepwise in both (X and Y) dimensions to achieve maximum signal voltage at detector 48. Final alignment aperture 46 is then closed again to ~⅓ of the diameter of probe beam 42. Pointing of second periscope mirror 78 is then fine adjusted to maximize power transmitted through final alignment aperture 46. If the needed adjustments are significant the procedure can be repeated multiple times. However, convergence to a collinear overlap is typically rapid because the ratio defined by the length of periscopes (70, 72 and 76, 78) compared to the distance from mirrors (72, 78) of last periscopes to first alignment aperture 44 is large. If first probe laser 32 needs to be realigned or 'optimized', the procedure from {step 7} is preferably followed rather than using mirror 62 from step 10 of the alignment procedure.

Next {step 8}, the separated probe beams (50, 52) resulting as $1^{st}$ order diffraction beams (50, 52) from holographic grating 18 are directed toward, and centered approximately on, folding minors (56, 58). Position and pointing of mirror 54 is also adjusted as needed. Folding mirrors (56, 58) direct separated probe beams (50, 52) into respective detectors (25, 26). After coarse centering, this final pointing is optimized, as is evidenced by the maximized signal received from detectors (25, 26).

Next {step 9}, the height of probe beams (36, 38) above surface of sample 10 is adjusted by translating the sample chamber 14 forward until sample 10 starts to clip probe beams (36, 38). This adjustment is observed as a ~50% reduction in signal from detectors (25, 26). Sample chamber 14 is then backed up approximately 2 mm so that probe beams (36, 38) pass freely to the center of vaporization plume 5.

Next {step 10}, the output beam 3 from ablation laser 1 is coarsely aligned and centered through optics (20, 22, 28, 6). Final focusing lens 6 is equipped with fine adjustment screws that allow the focal spot of ablation beam 1 to be positioned onto the XY plane of surface of sample 10. The X-position (horizontal) is not critical and is set to near the middle of sample 10. The Y-position (vertical) is preferably adjusted to within about 0.5 min of the position of probe beams (36, 38) by observation though view windows (not shown) positioned around ablation laser 1. Focusing lens 6 is also mounted on a linear translation stage 30 (not shown) that permits adjustment of the focal depth of the ablation laser 1 onto sample 10. Initial adjustment is done using a solid substrate 11 (not shown) (e.g., a vitreous carbon plate) blank, in which the focal depth of the vaporization plume 5 is adjusted (e.g., visually) to a point of maximum brightness. Alignment achieved using {Steps 8-10} provides suitable analytical signals and results (~10% precision). However, optimum instrument performance, accuracy, and precision (better than 1%) are obtained by aligning system 200 using actual reference materials in conjunction with an alignment and tune-up that are signal-based so as to maximize the detection signals.

If no mechanical changes have been made the system, only {step 7} (described hereinabove) need be applied to ensure that collinear alignment of both probe lasers (32, 34) is achieved. This is typically what is required on a day to day basis. If a solid substrate 11 is used to place a sample 10 that has a different thickness than that which is originally calibrated, {step 9} can be used to properly align and set the height of probe beams (36, 38) above surface of sample 10. Control and data acquisition software for systems 100 and 200 will now be described hereafter.

Figure 3:
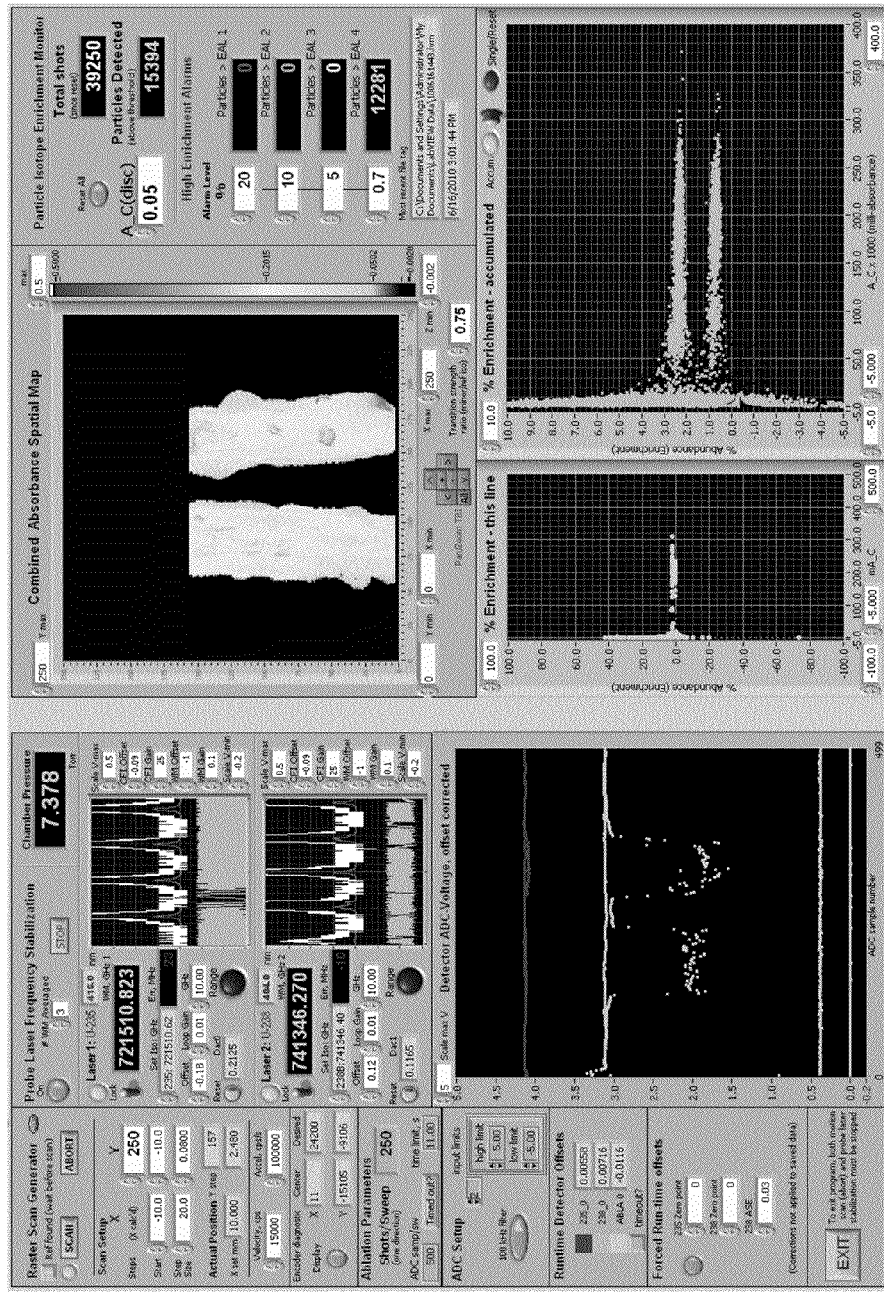
FIG. 3 is computer screen shot showing operation of the invention in one embodiment.

FIG. 3 illustrates a computer display showing various features of the performance of the method and system of the present invention. As demonstrated on the left hand side of this figure, the data regarding each of the laser probe beams are shown as is the rate of the raster scan, the ablation parameters and offset detector voltage. On the right hand side of the screenshot results of detected particles, a spatial map of the area and the percentage of accumulated enrichment are also shown. This configuration allows for easy ready access to information resulting from such scans.

The LAARS system described herein enables high-precision (sub 1% relative precision) in isotope ratio and relative isotope abundance measurements that provide at least a factor 10 better precision compared to standard laser-based ablation sample analysis systems known in the art. The invention minimizes systematic instrument errors and provides a precision suitable for destructive analysis. A first factor that provides for improved precision is precise collinear laser alignment. The precise collinear alignment assures that beams (36, 38) traverse the same volume of vaporization plume 5, which results in a significant reduction in noise that otherwise occurs due to spatial inhomogeneity of vaporization plume 5. Precise optical alignment of the two invention probe lasers ensures that the two diode laser beams are precisely collinear.

A second factor is the use of side-by-side unknown (termed UNK) and reference (termed REF) areas that provide rapidly interleaved spatial measurements in a timed-sequence format (not necessarily simultaneously), meaning that both a sample (unknown) and reference (calibration) measurement are collected for every line of a rasterized scan. This approach provides near real-time normalization of the instrument response, which corrects for systematic errors (including, e.g., laser frequency drift and pointing errors) that are problematic to, and characteristic of, laser-based systems.

A third factor is the use of two probe lasers tuned at different wavelengths, which allows simultaneous measurement of two distinct and different isotopes and determines and provides an isotope ratio on a shot-by-shot basis. Use of dual wavelength probe lasers 1): facilitates collinear alignment of two individual beams, which is essential for high precision measurements, and 2): provides measurement of two distinct and different isotopes using different atomic transitions. The dynamic range of these independent measurements can be significantly enhanced by using a strong transition for minor isotopes and a weaker transition for a major isotope. Shot-by-shot determinations further correct for variations in sample concentration and morphology, ablation yields, and plasma evolution dynamics, and are essential for precise ratio determinations due to the large variability in laser vaporization plumes with laser intensity and sample morphology. The probe lasers (32, 34) run at fixed wavelengths (no shifting between isotopes) and are amenable to probing plasmas from high-repetition-rate ablation lasers.

A fourth factor is the use of different atomic transitions for each isotope. Use of different transitions: a) allows probe lasers (32, 34) to operate at moderately to widely different wavelengths; b) use of distinct wavelengths permits simple combination and separation of probe laser beams (36, 38) before and after passing through the vaporization plume. For example, beams (36, 38) are easily combined with partially reflective mirrors 78, and separated again with a simple dispersive element 18 such as a diffraction grating or a prism, as detailed herein; c) wavelength multiplexing can be used to monitor multiple isotopes, including, multiple isotopes of different elements.

In addition, wavelength multiplexing provides the ability to include a 'non-resonant' background channel to correct absorption-like effects such as Schlieren distortions, and Rayleigh and Mie scattering that can substantially lower detection limits and reliability; d) use of atomic transitions that have different oscillator strengths can be used to effectively increase the dynamic range of the measurements. This approach is particularly useful for assay samples, e.g., where a signal from a major isotope can become opaque on a strong transition. This approach can also increase the precision for low-abundance measurements such as U-235 in natural or depleted uranium. A fifth factor is the use of optical isotope shifting, in which the shift is greater than the Doppler broadened width of the atomic transition in the laser vaporization plume. A sixth factor is the use of an ablation laser 1. Ablation laser 1 completely vaporizes sample 10 and requires no sample preparation. Samples 10 can be directly vaporized into a suitable chemical state, which eliminates sample loss and reduced sample analysis cost. A seventh factor is the use of a strongly laser absorbing substrate 11. Strong absorption of ablation radiation creates and ensures a strong and 'stable' vaporization plume 5.

Figure 4:
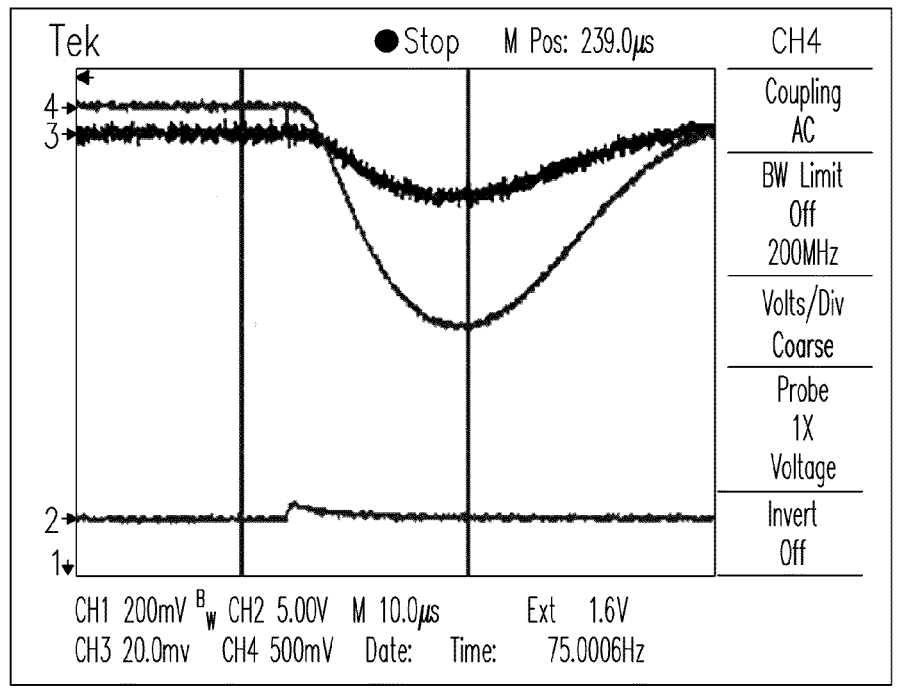
FIG. 4 shows transient absorption signals observed for LAARS measurement of low enriched uranium in accordance with the invention.

Various samples were analyzed utilizing the method and system of the present invention. FIGS. 4-9 show various examples of these tests. FIG. 4 shows the transient (probe laser) transmission signal for the minor U-235 (3.5% U-235) isotope, the transient (probe laser) transmission signal for the major U-238 isotope, and the signal for scattered ablation laser light are observed. Traces are shown on magnified, AC-coupled scales to allow the weak transmission signal for the minor U-235 isotope to be observed. At this scale, minor transmission signal is reduced to only 99.5% at the absorption maximum. Signal from scattered ablation laser light is stretched for visibility and further to provide a measurable signal at second timing pulse, described further herein. In the figure, sampling trigger (timing) pulses (vertical lines) used to precisely time the signal collection are also observed. Timing pulse corresponds to a non-absorbing transmission ($I_0$) before the firing of the ablation laser. Timing pulse corresponds to an absorbing ($I_t$) transmission at or near the transient minimum or absorption maximum. High precision (16 bit, 800 kHz, independent channels and gain) analog-to-digital conversions (ADC) are performed for each timing pulse. Transient transmission signals for both probe laser wavelengths are converted to transient absorbencies on a shot-by-shot basis, as given by Equation [1]:

$$A = -\log(I_t/I_o) \quad [1]$$

In accordance with the Beer-Lambert law, absorbencies are assumed proportional to isotope concentration. Isotope ratios are then calculated from Equation [2]:

$$R_{ij} = C_{imjn} * A_{im}/A_{jn} \quad [2]$$

Here, the ratio of isotope (i) to isotope (j) is proportional to the absorption for isotope (i) measured in transition (m) compared to that measured for isotope (l) in transition (n). In a binary mixture, the fractional abundance and percent (%) enrichment of the two isotopes are given by Equation [3]:

$$f_i = R_{ij}/(1+R_{ij}), \%E_i = 100 \cdot f_i \quad [3]$$

For uranium enrichment analysis, a binary mixture (U-235, U-238) is assumed, although traces of U-234 (natural decay product of U-238 at a natural abundance of 5.5 E$^{-5}$) are present in all samples, and more significant amounts of U-236 may be present in reprocessed nuclear fuel. At these conditions, linewidths are sufficiently narrow to resolve isotope structure for heavy metal elements, including, e.g., lanthanides and actinides. The invention thus provides the ability to characterize uranium isotope ratios (e.g., U-235:U-238) by subtle differences in atomic absorption wavelengths (e.g., for U-235 at 404.3 nm; and U-238 at 415.4 nm). The invention is also applicable to isotope ratio measurements involving elements with isotope shifts greater than the Doppler broadened linewidth of each isotope transition in the afterglow plasma. Transition frequencies and isotope shifts for selected isotopes are available from literature sources, which can be entered into the LAARS control program (described further herein) during instrument set-up. In cases where transition frequencies are not available, the LAARS instrument may be operated in a mode that scans a known wavelength from a first probe laser to obtain an isotope spectrum that directly determines a needed transition and an associated numeric laser frequency. A second probe laser is fixed on a reference isotope during the scan to normalize shot-by-shot fluctuations that occur during generation of vaporization plume by the ablation laser. Thus the LAARS system can be used effectively as a 'dual-beam isotope spectrometer' to yield high quality spectroscopic data, even in the presence of a noisy data source.

Figure 5:
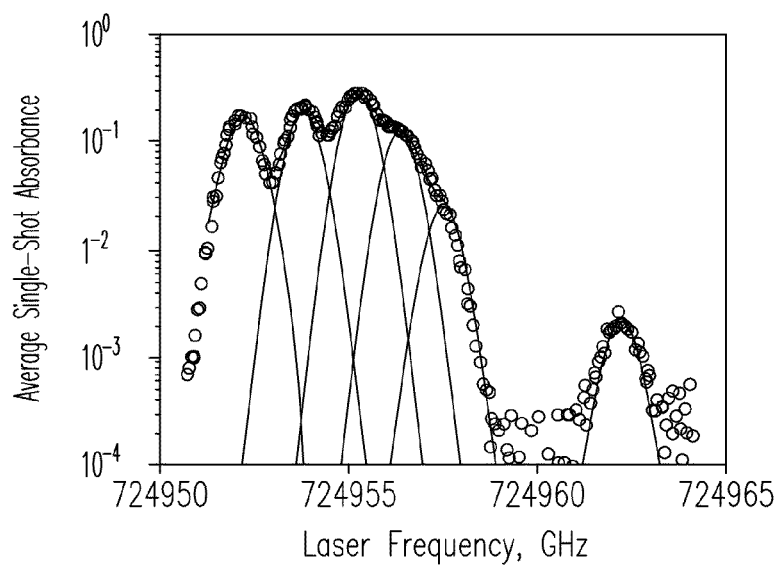
FIG. 5 shows a gadolinium isotope absorption spectrum measured by LAARS on the 413.4 nm line of gadolinium using a metallic foil target with natural isotopic abundances.

FIG. 5 shows a typical LAARS dual beam absorption spectrum collected for gadolinium (Gd). The spectrum was obtained using a metal foil target containing natural Gd isotope abundances using the 413.4 nm transition of Gd. For the analysis, the frequency of each probe laser was scanned slowly over the transition of interest (e.g., Gd-152, Gd-154 to Gd-158, and Gd-160), while the sample was continually rastered in order to provide fresh sample to the ablation laser. Transitions for each isotope can be further split into finer levels. Each point in the figure represents the observed signal averaged for 10 ablation shots, which accounts for nonlinearity in the laser scan. Frequency of each probe-laser at each point was read by a wavelength meter. In the figure, good fits are achieved for observed peaks with Gaussian lineshapes having equal width Gaussian profiles, which demonstrates that Doppler broadening (~0.8 GHz FWHM) is the dominant line-broadening factor.

Figure 6:
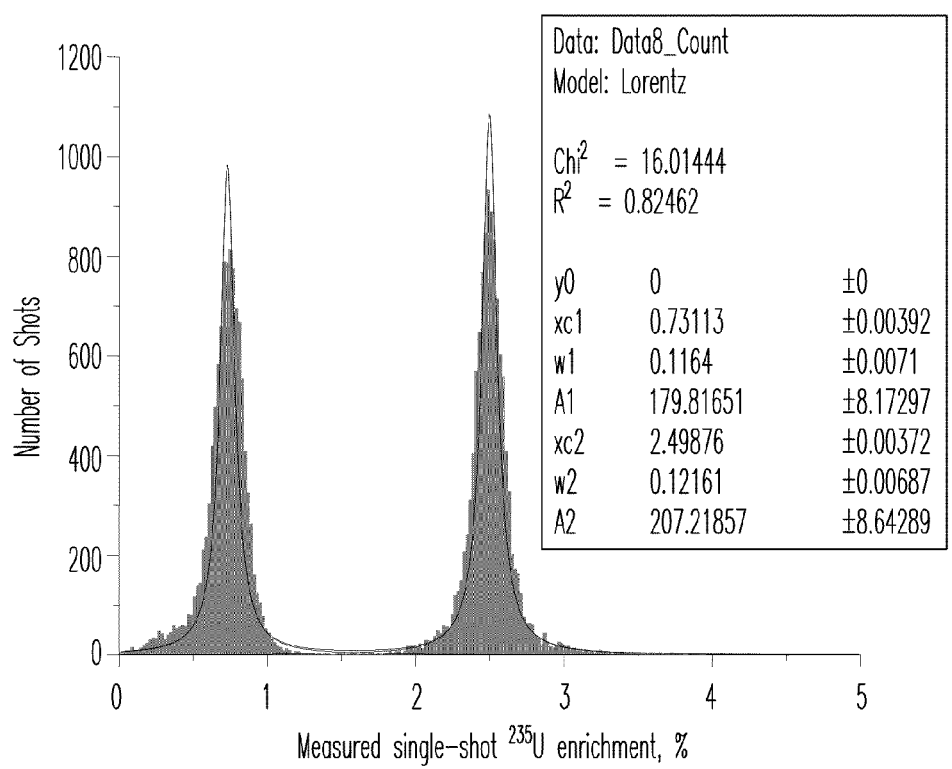
FIG. 6 is a histogram showing shot-by-shot U-235 enrichment analysis.

FIG. 6 is a histogram showing a cumulative U-235 isotope enrichment distribution showing shot-by-shot ratios (vertical scale) and elemental concentrations (horizontal scale) from data collected near the end of a LAARS analysis of a LEU sample that contained both a reference material with a known U-235 enrichment (3.547%) used for calibration and a sample unknown. Sample contained ~1 μg LEU painted as an aqueous solution of uranyl nitrate onto a vitreous carbon substrate. Data in the figure correspond to a single raster scan line. As shown in the figure, the two enrichment levels from the reference and unknowns are clearly seen. The reference (upper group of points) has roughly twice the signal intensity or elemental concentration (at ~3.5%) compared to the unknown. Cumulative results presented here were obtained from post experiment data processing.

Figure 7:
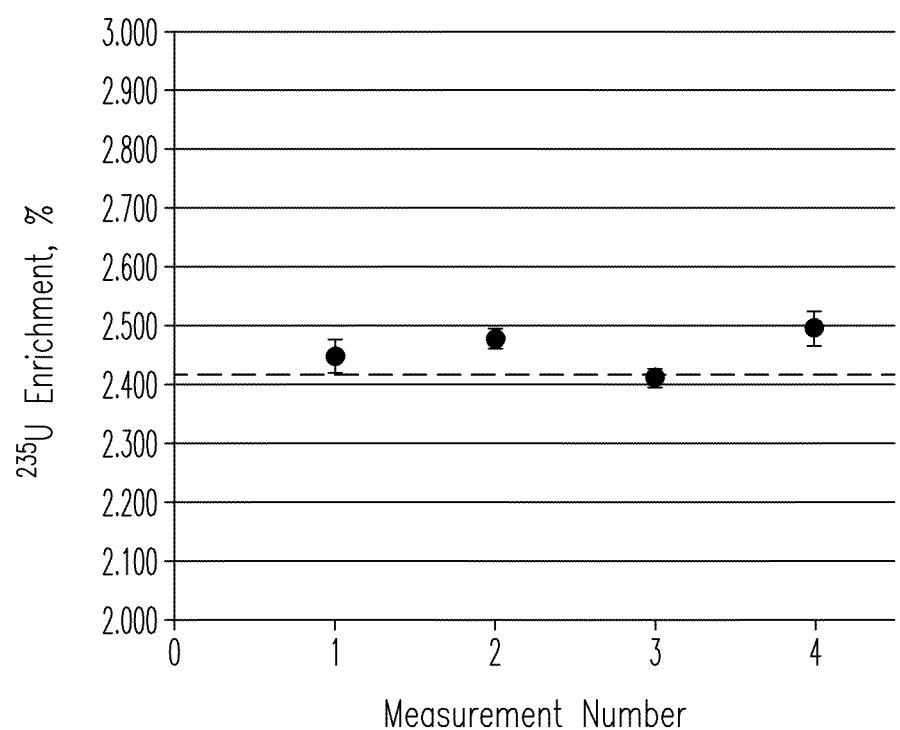
FIG. 7 is a plot showing precision and accuracy associated with repetitive, replicate analyses in accordance with the invention.

FIG. 7 is a plot showing results from four normalized LAARS Destructive (U-235) Analyses, with their associated accuracy and precision values from the replicate analyses. Results show the replicate LEU analyses have a precision below 1%. Measured U-235 enrichment values and uncertainties from replicate measurements are also presented for each sample. Measurements were made over several days with different sample loadings. Error bars demonstrate a 1σ uncertainty as determined from line-by-line statistical analyses. The dashed line presents the certified enrichment values for the 'unknown' sample.

Figure 8:
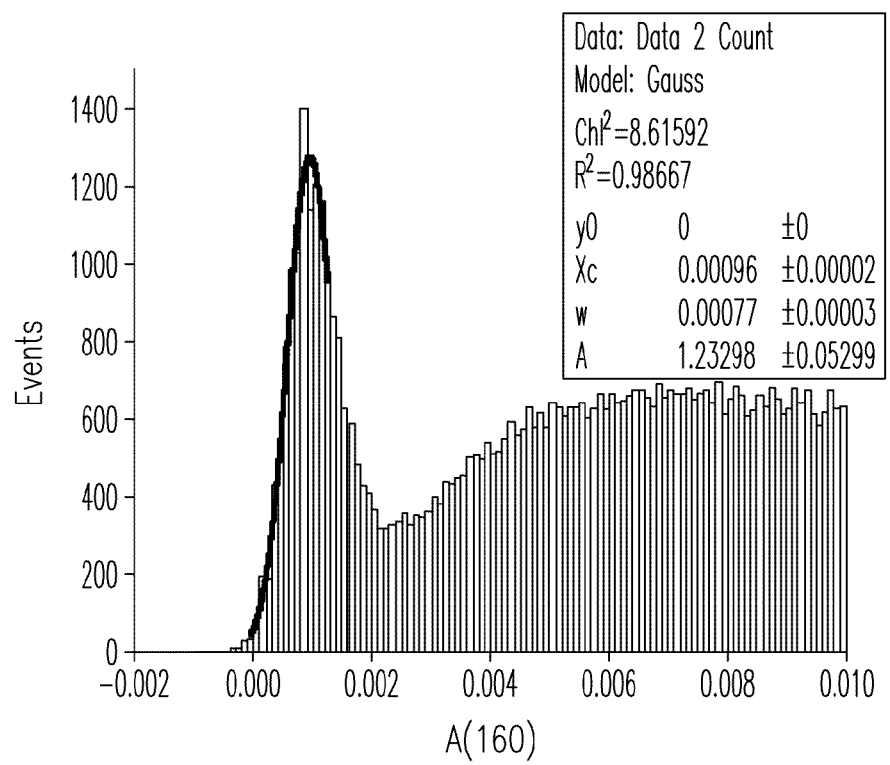
FIGS. 8 and 9 are zero-point offset and correction plots for a major isotope (Gd-160) and a minor isotope (Gd-152), collected in accordance with the invention.
Figure 9:
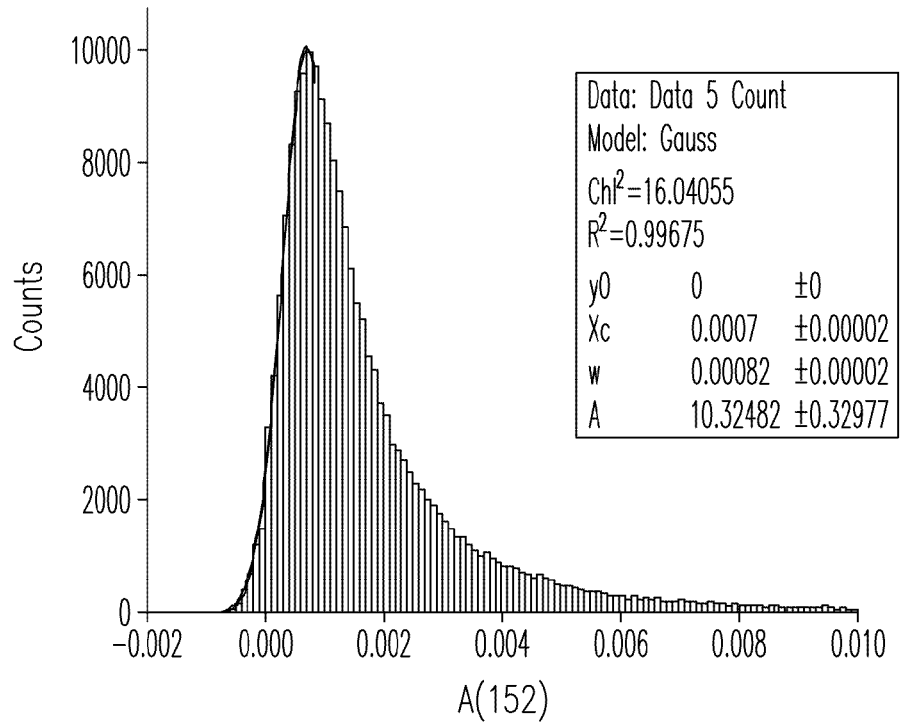

FIGS. 8 and 9 show zero-point offsets (12a) and baseline/matrix correction (12b) plots for a major gadolinium (Gd) isotope (i.e., Gd-160) and a minor isotope (i.e., Gd-152), respectively, measured with LAARS system 200. Absorption signal distributions are presented on a shot-by-shot basis for a sample 10 containing a moderate loading of Gd$_2$O$_3$ particles. In the figures, sharp peaks located at an absorbance (A) of ~0.0008 are attributed to shots where no particle is present. In FIG. 12a, the laser shots that contain the major isotope, Gd-160, exhibit higher absorbances and extend out to a maximum absorbance of ~0.5. In FIG. 12b, the minor isotope (0.9% relative abundance), Gd-152, has a much weaker absorbance. Thus, the particle distribution is poorly separated from the zero-particle peak.

Figure 10:
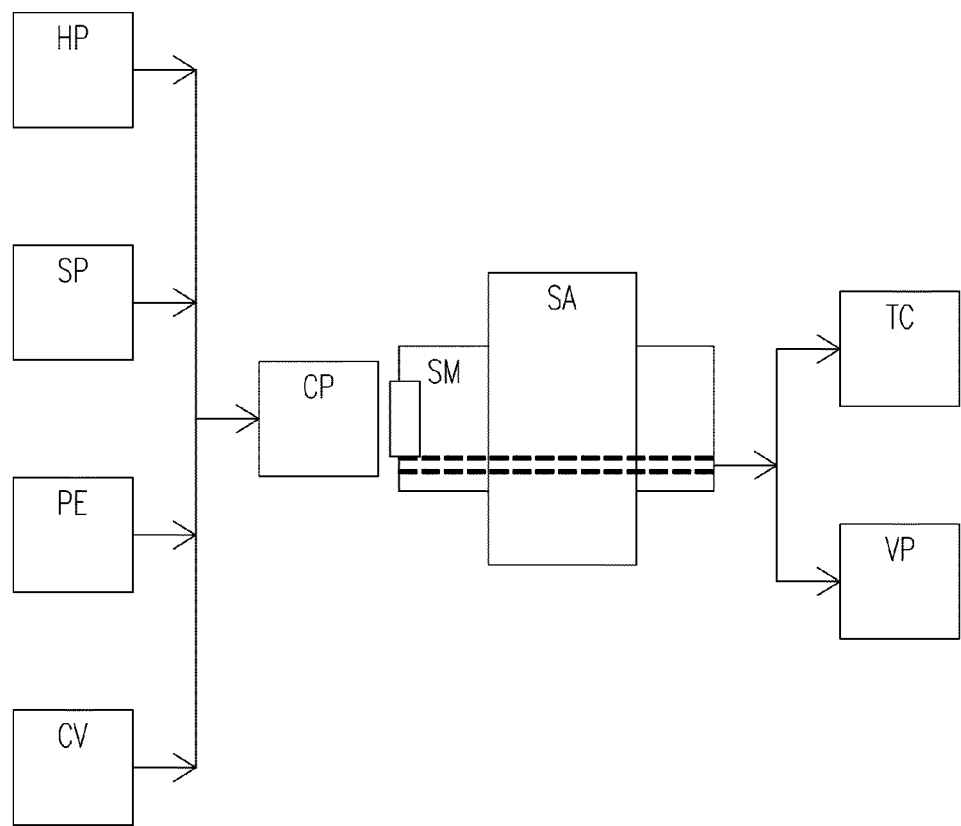
FIG. 10 is a schematic embodiment of a gaseous $UF_6$ sampling system.

FIG. 10 shows a schematic of one embodiment of a gaseous UF$_6$ sampling system. In operation, a sample media SM is inserted into the sampling assembly SA. In one embodiment the sample media SM is based on a chemisorption process for gaseous UF$_6$ uptake using solid sodium fluoride to form a stable, solid complex (2NaF—UF$_6$). The sample media can also be alumina sorbent (2Al$_2$O$_3$) that relies on the hydrolysis of UF$_6$ with available water with the alumina matrix, but with the less desirable production of hydrofluoric acid. The sampling assembly SA is attached to a gaseous UF$_6$ source connection point CP, such as a UF$_6$ cylinder valve CV, UF$_6$ processing equipment PE, a UF$_6$ sampling port SP, a UF$_6$ header pipe HP, or at other UF$_6$ access points. A small, portable vacuum pump VP is used to remove dead volume air from the sampling assembly SA connection point CP. Next, the NaF sample media SM is exposed to UF$_6$ at pressures typically between 1 to 50 Torr at around 30° C. This sampling media SM has an efficient loading ratio (UF$_6$/NaF weight) ranging from 0.6 to 0.8, allowing short exposure timescales to collect the required microgram sample needed for LAARS-DA analysis. The sampling assembly SA is removed from the connection point CP and the sampling media SM is transferred to the LAARS sample translation stage 12 shown in FIG. 1, where the solid complex (2NaF—UF$_6$) sample measured by LAARS to detection U-235 enrichment. In another embodiment the sampling assembly SA and the sample media SM are both directly transferred to the LAARS sample translation stage 12 shown in FIG. 1.

In yet another embodiment of FIG. 10, the sample media SM is based on a desublimation process for gaseous UF$_6$ uptake using cold finger (as known as a cold trap) to form solid UF$_6$. The sampling assembly SA is attached to a gaseous UF$_6$ source connection point CP, such as a UF$_6$ cylinder valve CV, UF$_6$ processing equipment PE, a UF$_6$ sampling port SP, a UF$_6$ header pipe HP, or at other UF$_6$ access points. A small, portable vacuum pump VP is used to remove dead volume air from the sampling assembly SA connection point CP. The cold finger temperature is maintained using a temperature controller TC. A reduced cold finger temperature is achieved using a Peltier junction device, dry ice, or liquid nitrogen. Next, the cold finger is exposed to $UF_6$ at pressures typically between 1 to 50 Torr at around 30° C. to condense $UF_6$ onto the cold finger. The sampling assembly SA is removed from the connection point CP and the sampling media SM, or alternatively the sampling assembly SA and the sample media SM, is transferred to the LAARS sample translation stage 12 shown in FIG. 1, where the condensed $UF_6$ is laser vaporized and the U-235 enrichment measured by LAARS.

These zero-point distributions represent weak background signals from the sample matrix and typically exhibit absorbances less than 0.001. In post measurement data processing, these zero-point distributions are fit with limited-range Gaussian functions to determine the actual center and width of the distribution. The fit range is limited from the low side to just over the top of the zero-point peak in order to minimize influence of true analyte signal on the zero-point peak fit. In this post analysis data reduction, the center of the distribution, corresponding to the average zero-point offset, is subtracted from each of the point-wise measured absorptions described above. This correction allows for obtaining accurate isotope ratios at low signal levels. The width of the zero-point distribution is also directly proportional to minimum detectable analyte absorbance, and hence detection limits.

As described above the LAARS system and method of the invention provide analyses of a wide variety of sample types. For example, the laser plasma provides in situ treatment that directly produces atoms/ions from a variety of sample types for subsequent absorption spectroscopy. Sample types include, but are not limited to, e.g., particulates, mixed sediment samples including, e.g., minerals, dusts, sediments, dirts; metal-containing samples; and other solid samples of various forms. Samples further include, but are not limited to, e.g., de-sublimated gases, dried liquids, aerodynamic particles, and other non-liquid or non-gaseous phase chemical compounds. The method is independent of chemical form, requires no pre- or post-vaporization sample preparation, and is compatible with de-sublimated gases, dried liquids, aerodynamic particles, and other solid forms of chemical compounds. Mixed sediment samples with dilute subject materials cause no analysis complications.

In one embodiment, gaseous uranium hexafluoride is collected by desublimation onto a cold finger within a reduced atmosphere chamber. In another embodiment, gaseous uranium hexafluoride is collected onto a chemical absorbent surface that binds the gaseous uranium hexafluoride thereto or that reacts through a chemisorption process, using solid chemical absorbent media (for example sodium fluoride) to yield a stable, solid complex (for example $2NaF-UF_6$).

Because of the aforementioned capabilities the present invention finds utility in a variety of applications that require relative isotope abundance measurements. Applications supporting the nuclear fuel cycle include, but are not limited to, uranium isotope (e.g., U-234, U-235, U-236, U-238) measurements during the various uranium extraction, enrichment, fuel production, and post-irradiation processes. The present invention finds particular nuclear utility where $UF_6$ (e.g., obtained from enrichment cascade equipment or cylinder equipment) is adsorbed onto surfaces suitable for LAARS measurements.

While the present invention has been described herein with reference to the preferred embodiments thereof, it should be understood that the invention is not limited thereto, and various alternatives in form and detail may be made therein without departing from the spirit and scope of the invention as defined in the following claims. Thus, no limitation in instrumentation or components is intended by the disclosure of the preferred embodiments. In addition, processes detailed herein can include additional steps without departing from the broader aspects of the present invention. All such components and/or modifications as would be envisioned, applied, practiced, or performed by the person of ordinary skill in the art are hereby incorporated. Further, while the invention is susceptible of various modifications and alternative constructions, it should be understood that there is no intention to limit the invention to the specific form disclosed, but, on the contrary, the invention covers all modifications, alternative constructions, and equivalents falling within the spirit and scope of the invention as defined in the claims.

We claim:

1. A method for high-precision isotope ratio measurement, the method comprising the steps of:
   generating a vapor plume containing at least two isotopes of the same or different atoms or molecular compounds, each isotope includes an isotope transition different and distinct from the other isotope;
   locking two wavelength-stabilized probe laser beams to respective wavelengths whereby each laser wavelength is separated a selected distance from the other wavelength with each laser wavelength fixed to a respective isotope transition line;
   forming a precisely collinear beam with the probe laser beams and directing same through the vapor plume such that the collinear beam traverses the same volume therein;
   measuring intensity of each laser beam at the selected wavelengths before and after generating the vapor plume; and
   determining the isotope ratio of the at least two isotopes based on the measured laser beam intensity at each wavelength.

2. The method of claim 1, wherein the measuring includes monitoring power of respective probe lasers as a function of time before and after generating the vapor plume, and measuring isotope absorbances when absorbances for the isotopes transitions are at a maximum.

3. The method of claim 1, wherein forming the precisely collinear beam includes optically combining and aligning the at least two laser beams.

4. The method of claim 1, wherein locking the probe laser beams includes laser beams having non-overlapping lines with a linewidth smaller than the atomic or molecular transition linewidths and the isotope shifts of the respective isotopes.

5. The method of claim 1, wherein one probe laser beam is tuned to a stronger atomic transition for a minor isotope and one probe laser beam is tuned to a weaker transition for a major isotope to increase the precision for low-abundance isotope measurements.

6. The method of claim 1, wherein generating the vapor plume includes generating a plasma and allowing the plasma to cool to provide a reservoir of gas-phase atomic species, molecular neutral species, and/or ion species representative of a sample material under measurement in the vapor plume.

7. The method of claim 1, wherein generating the vapor plume includes containing the vapor plume within an inert environment at a reduced pressure less than or equal to about 100 Torr to control the size and geometry of the vapor plume.

8. The method of claim 1, wherein generation of the vapor plume is by laser ablation.

9. The method of claim 1, wherein the vapor plume comprises an unknown component and a calibration reference to normalize and correct systematic errors during determination.

10. The method of claim 1, wherein the at least two isotopes in the vapor plume are U-235 and U-238.

11. The method of claim 1, wherein the vapor plume includes a sample containing uranium hexafluoride.

12. The method of claim 11, wherein the uranium hexafluoride is gaseous uranium hexafluoride collected with a chemical absorbent medium.

13. The method of claim 11, wherein the uranium hexafluoride is gaseous uranium hexafluoride collected by desublimation onto a cold finger.

14. The method of claim 1, wherein the vapor plume comprises isotopes selected from the group consisting of lanthanide isotopes, actinide isotopes, and combinations thereof.

15. The method of claim 1, wherein the vapor plume comprises isotopes with resolvable wavelength shifts larger than the Doppler-broadened linewidths of the respective isotope transitions.

16. The method of claim 1, further including separating the collinear beam into respective beams after directing same through the vapor plume.

17. The method of claim 1, wherein the isotope ratio has an uncertainty less than ±1%.

18. A system for high-precision isotope ratio measurement, the system comprising:
- an ablation laser configured to deliver a laser beam that vaporizes a sample containing at least two isotopes of the same or different atoms or molecular compounds forming a vapor plume, each isotope includes an isotope transition different and distinct from the other isotope;
- two wavelength-stabilized probe laser beams locked (tuned) to respective wavelengths whereby each laser wavelength is separated a selected distance from the other wavelength with each laser wavelength fixed to a respective isotope transition line;
- an alignment device or process configured to optically combine and align the at least two probe laser beams to form a precisely collinear beam that directs same through the vapor plume such that the collinear beam traverses the same volume of the vapor plume;
- a separator configured to separate the different wavelengths of the precisely collinear beam after transmission through the vapor plume; and
- at least two optical detectors configured to measure intensity of each laser beam at the selected isotope absorbance wavelengths for determination of the isotope ratio of the at least two isotopes.

19. The system of claim 18, wherein the isotope ratio has an uncertainty less than ±1%.

* * * * *